(12) United States Patent
Guedat et al.

(10) Patent No.: US 7,767,819 B2
(45) Date of Patent: Aug. 3, 2010

(54) THIAZOLYLIMIDAZOLE DERIVATIVES AND THEIR USE AS INHIBITORS OF MICROSOMAL TRIGLYCERIDE TRANSFER PROTEIN

(75) Inventors: Philippe Guedat, Toussieu (FR); Olivier Chevreuil, Condeissiat (FR); Thierry Convard, Sathonay-Camp (FR)

(73) Assignee: Merck Patent GmbH, Darmstadt (DE)

( * ) Notice: Subject to any disclaimer, the term of this patent is extended or adjusted under 35 U.S.C. 154(b) by 467 days.

(21) Appl. No.: 10/587,975

(22) PCT Filed: Jan. 17, 2005

(86) PCT No.: PCT/EP2005/000388

§ 371 (c)(1), (2), (4) Date: Aug. 3, 2006

(87) PCT Pub. No.: WO2005/074934

PCT Pub. Date: Aug. 18, 2005

(65) Prior Publication Data

US 2008/0214610 A1    Sep. 4, 2008

(30) Foreign Application Priority Data

Feb. 4, 2004    (FR) ................... 04 01046

(51) Int. Cl.
C07D 417/04 (2006.01)
A61K 31/4535 (2006.01)
(52) U.S. Cl. .................. 546/209; 546/194; 514/318; 514/326
(58) Field of Classification Search .......... 514/318, 514/326; 546/194, 209
See application file for complete search history.

(56) References Cited

U.S. PATENT DOCUMENTS

2003/0170858 A1 * 9/2003 Charifson et al. .......... 435/199
2004/0034028 A1   2/2004 Guevel et al.

FOREIGN PATENT DOCUMENTS

WO     WO 0152845    * 7/2001
WO     WO 02/42291 A   5/2002

OTHER PUBLICATIONS

Dorwald F. A. Side Reactions in Organic Synthesis, 2005, Wiley: VCH, Weinheim p. IX of Preface p. 1-15, 41.*
Chang et. al. "Microsomal triglyceride transfer protein (MTP) inhibitors: Discovert of clinically active inhibitorsusing high-throughput screening and parallel synthesis paradigms" Current Opinion in Drug Discovery and Development 2002, 5, 562-570.*
Claibourne et. al. "An Efficient Synthesis of Tetrasubstituted Imidazoles from N-(2-Oxo)-amides" Tetrahedron Letters 1998, 39, 8939-8942.*
Magnin, D. R. et al. "Microsomal Triglyceride Transfer Protein Inhibitors: Discovery and Synthesis of Alkyl Phosphonates as Potent MTP Inhibitors and Cholesterol Lowering Agents" Bioorganic & Medicinal Chemistry Letters 2003, 13, 1337-1340.*
Ksander et al. "Diaminoindanes as Microsomal Triglyceride Transfer Protein Inhibitors" Journal of Medicinal Chemistry, 2001, 44, 4677-4687.*
Peukert et. al. "Identification and structure-activity relationships of ortho-biphenyl carboxamides as potent Smoothened antagonists inhibiting the Hedgehog signaling pathway" Bioorganic & Medicinal Chemistry Letters 2009, 19, 328-331.*
West, Anthony R., Solid State Chemistry and its Applications, Wiley, New York, 1988, pp. 358 & 365.*

* cited by examiner

Primary Examiner—Rita J Desai
Assistant Examiner—David K O'Dell
(74) Attorney, Agent, or Firm—Millen, White, Zelano, Branigan, P.C.

(57) ABSTRACT

The present invention relates to thiazolylimidazole derivatives of the general formula (I) in which: G represents a bond or a divalent radical chosen from the groups g1, g2 and g3; and $R^1$, $R^2$, $R^3$, $R^4$, $R^5$, $R^6$, Y and Z are as defined in the description. Application of the compounds of the formula (I) to the treatment of hypertriglyceridaemia, hypercholesterolaemia and dyslipidaemia.

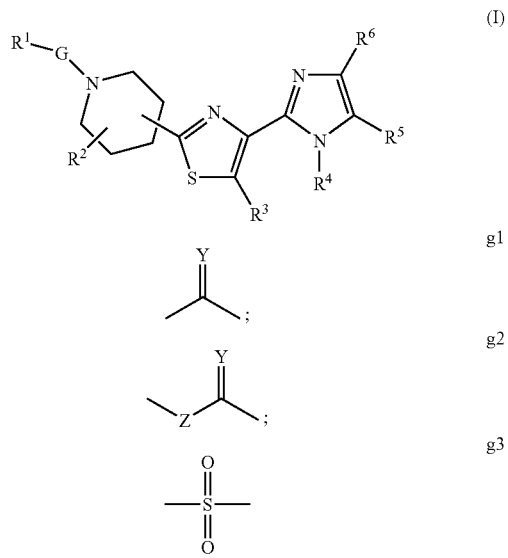

3 Claims, No Drawings

THIAZOLYLIMIDAZOLE DERIVATIVES AND THEIR USE AS INHIBITORS OF MICROSOMAL TRIGLYCERIDE TRANSFER PROTEIN

The invention relates to compounds that are inhibitors of microsomal triglyceride transfer protein (MTP), to pharmaceutical compositions comprising them, and to the use thereof in medicine.

MTP (microsomal triglyceride transfer protein) is a transfer protein located in the reticulum of hepatocytes and enterocytes which catalyses the assembly of biomolecules that transport triglycerides, the apo B lipoproteins.

The term apo B more particularly denotes apoprotein 48 of the intestine and apoprotein 100 of the liver.

Mutations in MTP or in the B apoproteins are reflected in man by very low levels or even an absence of apo B lipoproteins. The lipoproteins containing apo B (chylomicrons, Very Low Density Lipoproteins) and their metabolic residues (chylomicron remnants, Low Density Lipoproteins) are recognized as being a major risk factor in the development of atherosclerosis, a major cause of death in industrialized countries.

It is observed that, in individuals who are heterozygous for these mutations, levels reduced on average by a half are associated with a low cardiovascular risk (C. J. Glueck, P. S. Gartside, M. J. Mellies, P. M. Steiner, *Trans. Assoc. Am. Physicians*, 90, 184 (1977)). This suggests that modulation of the secretions of triglyceride-rich lipoproteins by means of MTP antagonists and/or of secretion of apo B might be useful in the treatment of atherosclerosis and more broadly of pathologies characterized by an increase in apo B lipoproteins.

Molecules that inhibit MTP and/or the secretion of apo B might thus be useful for the treatment of diabetes-related hypertriglyceridaemia, hypercholesterolaemia and dyslipidaemia, and also for the prevention and treatment of obesity.

Molecules of thiazolylpiperidine structure having an inhibitory activity on MTP and/or on apoB secretion form the subject of the as yet unpublished French patent application FR 03 07670.

It has now been discovered that other novel compounds with a structure of thiazolylimidazole type also have inhibitory properties on MTP and/or on apoB secretion. As a result of this activity, these novel compounds have an entirely advantageous possible application in the treatment of diabetes-related hypertriglyceridaemia, des hypercholesterolaemia and dyslipidaemia, and also in the prevention and treatment of obesity.

Thus, the present invention relates firstly to the compounds of thiazolylimidazole structure of the general formula (I):

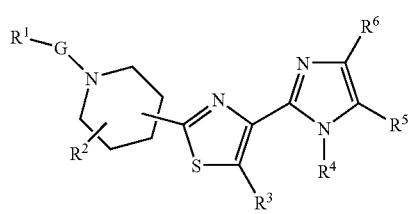

in which:

G represents a bond or a divalent radical chosen from the groups g1, g2 and g3 below:

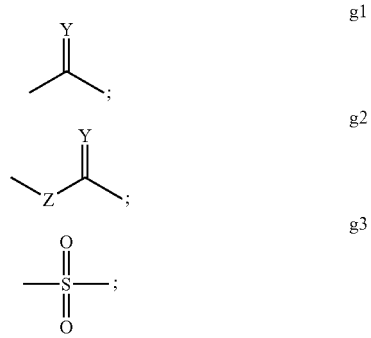

$R^1$ is chosen from hydrogen and an alkyl, alkenyl, alkynyl, cycloalkyl, heterocycloalkyl, aryl, heteroaryl, alkylcarbonyl or alkoxycarbonyl radical;

$R^2$ and $R^3$, which may be identical or different, are chosen, independently of each other, from a hydrogen atom, an alkyl, alkenyl, alkynyl, cycloalkyl, heterocycloalkyl, aryl or heteroaryl radical and a radical —NRR';

$R^4$, $R^5$ and $R^6$, which may be identical or different, are chosen, independently of each other, from a hydrogen atom and an alkyl, alkenyl, alkynyl, cycloalkyl, heterocycloalkyl, aryl or heteroaryl radical;

R and R', which may be identical or different, represent, independently of each other, a hydrogen atom or a radical chosen from alkyl, alkenyl, alkynyl, cycloalkyl, heterocycloalkyl, aryl and heteroaryl; or together form, with the nitrogen atom that bears them, a heterocycle, or together form the double bond of an alken-1-yl radical;

Y represents an oxygen or sulfur atom; and

Z represents —NH— or an oxygen atom;

the possible geometrical and/or optical isomers, epimers and various tautomeric forms, and possible oxidized forms, especially amine oxides, thereof, the solvates and the hydrates of these compounds;

and also the possible pharmaceutically acceptable salts thereof with an acid or a base, or the pharmaceutically acceptable prodrugs of these compounds.

The definitions that follow specify the natures of the various groups and radicals defined above. Unless otherwise mentioned, these definitions apply for all the terms of the present invention thus explained.

The term "halogen atom" denotes a fluorine, chlorine, bromine or iodine atom.

The term "alkyl" denotes a linear or branched alkyl radical containing from 1 to 12 carbon atoms, optionally substituted by one or more chemical species, which may be identical or different, chosen from a halogen atom, an oxo, thioxo, hydroxyl, thiol, —NRR' (where R and R', which may be identical or different, are as defined above), cyano, nitro or carboxyl group, and an alkoxy, alkenyloxy, alkynyloxy, alkylthio, alkyldisulfanyl (alkyl-S—S—), alkylsulfinyl (alkyl-S (=O)—), alkylsulfonyl (alkyl-S(=O)$_2$—), alkenylthio, alkynylthio, alkylcarbonyl, alkoxycarbonyl, alkylcarbonylamino, alkoxycarbonylamino, arylcarbonyl, arylcarbonylamino, (di)alkylaminocarbonyl, cycloalkyl, cycloalkoxy, cycloalkylthio, heterocycloalkyl, heterocycloalkoxy, heterocycloalkylthio, aryl, aryloxy, arylthio, heteroaryl, heteroarylcarbonyl, heteroaryloxy or heteroarylthio radical.

Examples of alkyl radicals, which may be optionally substituted as indicated above, are methyl, ethyl, propyl, isopropyl, butyl, isobutyl, tert-butyl, pentyl, isopentyl, neopentyl, 2-methylbutyl, 1-ethylpropyl, hexyl, isohexyl, neohexyl, 1-methylpentyl, 3-methylpentyl, 1,1-dimethylbutyl, 1,3-dimethylbutyl, 1-ethylbutyl, 1-methyl-1-ethylpropyl, heptyl, 1-methylhexyl, 1-propylbutyl, 4,4-dimethylpentyl, octyl, 1-methylheptyl, 2-methylhexyl, 5,5-dimethylhexyl, nonyl, decyl, 1-methylnonyl, 3,7-dimethyloctyl and 7,7-dimethyloctyl.

The term "alkenyl" denotes a linear or branched alkyl radical comprising at least one unsaturation in double bond form and containing from 2 to 12 carbon atoms, optionally substituted by one or more chemical species, which may be identical or different, chosen from a halogen atom, an oxo, thioxo, hydroxyl, thiol, —NRR' (in which R and R', which may be identical or different, are as defined above), cyano, nitro or carboxyl group, and an alkoxy, alkenyloxy, alkynyloxy, alkylthio, alkyldisulfanyl (alkyl-S—S—), alkylsulfinyl (alkyl-S(=O)—), alkylsulfonyl (alkyl-S(=O)$_2$—), alkenylthio, alkynylthio, alkylcarbonyl, alkoxycarbonyl, alkylcarbonylamino, alkoxycarbonylamino, arylcarbonyl, arylcarbonylamino, (di)alkylaminocarbonyl, cycloalkyl, cycloalkoxy, cycloalkylthio, heterocycloalkyl, heterocycloalkoxy, heterocycloalkylthio, aryl, aryloxy, arylthio, heteroaryl, heteroarylcarbonyl, heteroaryloxy or heteroarylthio radical.

Examples of alkenyl radicals, which may be optionally substituted as indicated above, are ethylenyl, propenyl, propadienyl, butenyl, butadienyl, pentenyl, pentadienyl, hexenyl, hexadienyl, heptenyl, heptadienyl, octenyl, octadienyl, nonenyl, nonadienyl, decenyl and decadienyl, and also the branched isomers thereof, the absence of indication of the position of the double bond(s) being necessarily understood as meaning that no limitation is placed on the double bond(s). For example, the "pentenyl" radical includes, without preference, the pent-1-en-1-yl, pent-2-en-1-yl and pent-3-en-1-yl radicals, but also the pent-1-en-2-yl, pent-2-en-2-yl and pent-3-en-2-yl radicals, as well as the pent-1-en-3-yl, pent-2-en-3-yl and pent-3-en-3-yl radicals.

The term "alkynyl" denotes a linear or branched alkyl radical comprising at least one unsaturation in triple bond form and containing from 2 to 12 carbon atoms, optionally substituted by one or more chemical species, which may be identical or different, chosen from a halogen atom, an oxo, thioxo, hydroxyl, thiol, —NRR' (in which R and R', which may be identical or different, are as defined above), cyano, nitro or carboxyl group, and an alkoxy, alkenyloxy, alkynyloxy, alkylthio, alkyldisulfanyl (alkyl-S—S—), alkylsulfinyl (alkyl-S(=O)—), alkylsulfonyl (alkyl-S(=O)$_2$—), alkenylthio, alkynylthio, alkylcarbonyl, alkoxycarbonyl, alkylcarbonylamino, alkoxycarbonylamino, arylcarbonyl, arylcarbonylamino, (di)alkylaminocarbonyl, cycloalkyl, cycloalkoxy, cycloalkylthio, heterocycloalkyl, heterocycloalkoxy, heterocycloalkylthio, aryl, aryloxy, arylthio, heteroaryl, heteroarylcarbonyl, heteroaryloxy or heteroarylthio radical.

Examples of alkynyl radicals, which may be optionally substituted as indicated above, are ethynyl, propynyl, propadiynyl, butynyl, butadiynyl, pentynyl, pentadiynyl, hexynyl, hexadiynyl, heptynyl, heptadiynyl, octynyl, octadiynyl, nonynyl, nonadiynyl, decynyl and decadiynyl, and also the branched isomers thereof, the absence of indication of the position of the double bond(s) being necessarily understood as meaning that no limitation is placed on the double bond(s). For example, the "pentynyl" radical includes, without preference, the pent-1-yn-1-yl, pent-2-yn-1-yl and pent-3-yn-1-yl radicals, but also the pent-1-yn-2-yl, pent-2-yn-2-yl and pent-3-yn-2-yl radicals, as well as the pent-1-yn-3-yl, pent-2-yn-3-yl and pent-3-yn-3-yl radicals.

The term "cycloalkyl" denotes a monocyclic, bicyclic or tricyclic, bridged or unbridged cycloalkyl radical containing from 3 to 13 carbon atoms, optionally comprising one or more double bonds, also including spirane compounds, and optionally substituted by one or more chemical species, which may be identical or different, chosen from a halogen atom, an oxo, thioxo, hydroxyl, thiol, —NRR' (in which R and R', which may be identical or different, are as defined above), cyano, nitro or carboxyl group, and an alkyl, especially substituted by one or more halogen atoms, in particular perhaloalkyl, for instance trifluoromethyl, alkenyl, alkynyl, alkoxy, alkenyloxy, alkynyloxy, alkylthio, alkyldisulfanyl (alkyl-S—S—), alkylsulfinyl (alkyl-S(=O)—), alkylsulfonyl (alkyl-S(=O)$_2$—), alkenylthio, alkynylthio, alkylcarbonyl, alkoxycarbonyl, alkylcarbonylamino, alkoxycarbonylamino, arylcarbonyl, arylcarbonylamino, (di)alkylaminocarbonyl, cycloalkyl, cycloalkoxy, cycloalkylthio, heterocycloalkyl, heterocycloalkoxy, heterocycloalkylthio, aryl, aryloxy, arylthio, heteroaryl, heteroarylcarbonyl, heteroaryloxy or heteroarylthio radical.

Examples of cycloalkyl groups, which are optionally substituted as indicated above, are especially cyclopropyl, cyclobutyl, cyclopentyl, cyclohexyl, cycloheptyl, cyclooctyl and cyclodecyl, adamantyl, diamantyl, norbornyl and bornyl groups.

The term "heterocycloalkyl" denotes a monocyclic, bicyclic or tricyclic radical containing a total of from 3 to 13 atoms, among which 1, 2, 3 or 4 are chosen, independently of each other, from nitrogen, oxygen and sulfur, the other atoms being carbon atoms, the said heterocyclic radical also optionally comprising 1, 2, 3 or 4 double bonds, also including spirane compounds, and being optionally substituted by one or more chemical species, which may be identical or different, chosen from a halogen atom, an oxo, thioxo, hydroxyl, thiol, —NRR' (in which R and R', which may be identical or different, are as defined above), cyano, nitro or carboxyl group, and an alkyl, especially substituted by one or more halogen atoms, in particular perhaloalkyl, for instance trifluoromethyl, alkenyl, alkynyl, alkoxy, alkenyloxy, alkynyloxy, alkylthio, alkyldisulfanyl (alkyl-S—S—), alkylsulfinyl (alkyl-S(=O)—), alkylsulfonyl (alkyl-S(=O)$_2$—), alkenylthio, alkynylthio, alkylcarbonyl, alkoxycarbonyl, alkylcarbonylamino, alkoxycarbonylamino, arylcarbonyl, arylcarbonylamino, (di)alkylaminocarbonyl, cycloalkyl, cycloalkoxy, cycloalkylthio, heterocycloalkyl, heterocycloalkoxy, heterocycloalkylthio, aryl, aryloxy, arylthio, heteroaryl, heteroarylcarbonyl, heteroaryloxy or heteroarylthio radical.

In particular, saturated or partially unsaturated, monocyclic heterocycles of 5 to 8 atoms are saturated, or partially unsaturated, derivatives of the heteroaryls defined later. More particularly, among the heterocycloalkyl radicals that may be mentioned are morpholino, morpholinyl, piperidyl, thiazolidinyl, oxazolidinyl, tetrahydrothienyl, tetrahydrofuryl, tetrahydropyranyl, pyrrolidinyl, isoxazolidinyl, imidazolidinyl and pyrazolidinyl radicals.

The term "aryl" denotes a monocyclic, bicyclic or tricyclic aryl radical containing from 6 to 14 carbon atoms, optionally substituted by one or more chemical species, which may be identical or different, chosen from a halogen atom, a hydroxyl, thiol, —NRR' (in which R and R', which may be identical or different, are as defined above), cyano, nitro or carboxyl group, and an alkyl, especially substituted by one or more halogen atoms, in particular perhaloalkyl, for instance trifluoromethyl, alkenyl, alkynyl, alkoxy, alkenyloxy, alkynyloxy, alkylthio, alkyldisulfanyl (alkyl-S—S—), alkylsulfinyl (alkyl-S(=O)—), alkylsulfonyl (alkyl-S(=O)$_2$—), alkenylthio, alkynylthio, a phosphoric acid derivative [(alkyl-0)$_2$—P—O-alkyl], alkylcarbonyl, alkoxycarbonyl, alkylcarbonylamino, alkoxycarbonylamino, arylcarbonyl, arylcarbonylamino, (di)alkylaminocarbonyl, cycloalkyl, cycloalkoxy, cycloalkylthio, heterocycloalkyl, heterocycloalkoxy, heterocycloalkylthio, aryl, aryloxy, arylthio, heteroaryl, heteroarylcarbonyl, heteroaryloxy or heteroarylthio radical.

Aryl radicals that may be mentioned, in a non-limiting manner, include phenyl, naphthyl, anthryl and phenanthryl radicals.

The term "heteroaryl" denotes a monocyclic, bicyclic or tricyclic aromatic radical containing a total of from 3 to 13 atoms, among which 1, 2, 3 or 4 are chosen, independently of each other, from nitrogen, oxygen and sulfur, optionally in oxidized form (in the case of nitrogen and sulfur), the other atoms being carbon atoms, the said heteroaryl radical being optionally substituted by one or more chemical species, which may be identical or different, chosen from a halogen atom, a hydroxyl, thiol, —NRR' (in which R and R', which may be identical or different, are as defined above), cyano, nitro or carboxyl group, and an alkyl, especially substituted by one or more halogen atoms, in particular perhaloalkyl, for instance trifluoromethyl, alkenyl, alkynyl, alkoxy, alkenyloxy, alkynyloxy, alkylthio, alkyldisulfanyl (alkyl-S—S—), alkylsulfinyl (alkyl-S(═O)—), alkylsulfonyl (alkyl-S(═O)$_2$—), alkenylthio, alkynylthio, alkylcarbonyl, alkoxycarbonyl, alkylcarbonylamino, alkoxycarbonylamino, arylcarbonyl, arylcarbonylamino, (di)alkylaminocarbonyl, cycloalkyl, cycloalkoxy, cycloalkylthio, heterocycloalkyl, heterocycloalkoxy, heterocycloalkylthio, aryl, aryloxy, arylthio, heteroaryl, heteroarylcarbonyl, heteroaryloxy or heteroarylthio radical.

Preferably, at least one of the monocycles constituting the heterocycle contains from 1 to 4 endocyclic hetero atoms and more preferably from 1 to 4 endocyclic hetero atoms. According to the invention, the heterocyclic polycyclic nucleus consists of one or more monocycles each containing from 5 to 8 atoms included in the ring.

Examples of heteroaryl radicals, optionally substituted as has just been described, are radicals derived from heteroaromatic compounds, such as pyridine, furan, thiophene, pyrrole, imidazole, thiazole, isothiazole, isoxazole, furazane, pyridazine, pyrimidine, pyrazine, thiazines, oxazole, pyrazole, oxadiazole, triazole and thiadiazole. Among the preferred heteroaryls that may be mentioned are pyridyls, pyrimidinyls, triazolyls, thiadiazolyls, oxazolyls, thiazolyls and thienyls.

Examples of bicyclic heteroaryl radicals in which each monocycle contains from 5 to 8 endocyclic atoms are derived from aromatic compounds chosen from indolizine, indole, isoindole, benzofuran, benzothiophene, indazole, benzimidazole, benzothiazole, benzofurazane, benzothiofurazane, purine, quinoline, isoquinoline, cinnoline, phthalazine, quinazoline, quinoxaline, naphthyridines, pyrazolotriazines, pyrazolopyrimidine and pteridine.

Among the heteroaryls defined above, quinolyl, pyridyl, benzotriazolyl, triazolyl, acridyl, phenazinyl and carbazolyl radicals are preferred.

For the compounds of the formula (I) presented above, the term "geometrical isomer" means a cis/trans or E/Z isomerism. More particularly, the possible double bond(s) present in the various substituents of the compounds of the general formula (I) may be of E or Z configuration. These pure or impure geometrical isomers, alone or as a mixture, form an integral part of the compounds of the formula (I).

The term "optical isomer" includes all the isomeric forms, alone or as mixtures, resulting from the presence of one or more axes and/or centres of symmetry in the molecule, and resulting in rotation of a beam of polarized light. The term "optical isomer" more particularly includes enantiomers and disasteroisomers, in pure form or as a mixture.

The acids capable of forming pharmaceutically acceptable salts with the compounds of the formula (I) above are organic or mineral acids. Non-limiting examples that may be mentioned include hydrochloric acid, hydrobromic acid, phosphoric acid, sulfuric acid, tartaric acid, citric acid, maleic acid, acetic acid, fumaric acid, alkanesulfonic acid, naphthalenesulfonic acid, para-toluenesulfonic acid, bistrifluoroacetic acid and camphoric acid.

The bases capable of forming pharmaceutically acceptable salts with the compounds of the formula (I) above are mineral or organic bases. Among these bases, non-limiting examples that may be mentioned include sodium hydroxide, potassium hydroxide, ammonia, diethylamine, triethylamine, ethanolamine, diethanolamine, piperidine, piperazine, morpholine, basic amino acids, such as arginine and lysine, osamines, for example meglumine, and amino alcohols, such as 3-aminobutanol and 2-aminobutanol.

The invention especially covers the pharmaceutically acceptable salts, as indicated above, but also salts allowing a suitable separation or crystallization of the compounds of the formula (I), such as the salts obtained with chiral amines, The compounds of the formula (I) above also comprise the prodrugs of these compounds.

The term "prodrugs" means compounds which, once administered to the patient, are chemically and/or biologically converted by the living body, into compounds of the formula (I).

Among the compounds of the formula (I) according to the invention that are preferred are those for which the radical $R^2$ represents hydrogen, the other substituents being as defined above, the possible geometrical and/or optical isomers, epimers and various tautomeric forms, and optional oxidized forms, especially amine oxides, thereof, and the solvates and hydrates of these compounds;

and also the possible pharmaceutically acceptable salts thereof with an acid or a base, or the pharmaceutically acceptable prodrugs of these compounds.

Preference is also given to the compounds of the formula (I) according to the invention for which the radical $R^3$ represents hydrogen, the other substituents being as defined above, the possible geometrical and/or optical isomers, epimers and various tautomeric forms, and optional oxidized forms, especially amine oxides, thereof, and the solvates and hydrates of these compounds;

and also the possible pharmaceutically acceptable salts thereof with an acid or a base, or the pharmaceutically acceptable prodrugs of these compounds.

Another preferred group of compounds according to the present invention consists of compounds of the general formula (I) in which the radicals $R^4$ and $R^5$, independently of each other, represent an alkyl radical, the other substituents being as defined above, the possible geometrical and/or optical isomers, epimers and various tautomeric forms, and optional oxidized forms, especially amine oxides, thereof, and the solvates and hydrates of these compounds;

and also the possible pharmaceutically acceptable salts thereof with an acid or a base, or the pharmaceutically acceptable prodrugs of these compounds.

Another preferred group of compounds according to the present invention consists of compounds of the general formula (I) in which the radical $R^6$ represents an aryl or heteroaryl radical, the other substituents being as defined above, the possible geometrical and/or optical isomers, epimers and various tautomeric forms, and optional oxidized forms, especially amine oxides, thereof, and the solvates and hydrates of these compounds;

and also the possible pharmaceutically acceptable salts thereof with an acid or a base, or the pharmaceutically acceptable prodrugs of these compounds.

Another preferred group of compounds according to the present invention consists of compounds of the formula (I) in which the thiazolyl radical is branched in position 3 or in position 4 of the piperidine nucleus, preferably in position 4 of the piperidine nucleus.

Another preferred group of compounds according to the present invention consists of compounds of the general formula (I) in which G represents the radical g1, preferably in which Y represents an oxygen atom, the other substituents being as defined above, the possible geometrical and/or optical isomers, epimers and various tautomeric forms, and optional oxidized forms, especially amine oxides, thereof, and the solvates and hydrates of these compounds;

and also the possible pharmaceutically acceptable salts thereof with an acid or a base, or the pharmaceutically acceptable prodrugs of these compounds.

Another preferred group of compounds according to the present invention consists is of compounds of the general formula (I) in which the radicals $R^2$ and $R^3$ each represent a hydrogen atom, the radicals $R^4$ and $R^5$ represent, independently of each other, an alkyl radical, the radical $R^6$ represents an aryl or heteroaryl radical, the thiazolyl radical is branched in position 4 of the piperidine nucleus, and G represents the radical g1 in which Y represents an oxygen atom, the other substituents being as defined above, the possible geometrical and/or optical isomers, epimers and various tautomeric forms, and optional oxidized forms, especially amine oxides, thereof, and the solvates and hydrates of these compounds;

and also the possible pharmaceutically acceptable salts thereof with an acid or a base, or the pharmaceutically acceptable prodrugs of these compounds.

Another preferred group of compounds of the invention consists of compounds of the general formula (I) in which $R^1$ represents an aryl radical, especially phenyl, substituted by one or more aryl and/or alkyl radicals.

The compounds of the general formula (I) in which $R^1$ represents a biphenyl radical, optionally substituted by one or more alkyl radicals, preferably methyl, ethyl or propyl, and/or with a perhaloalkyl or perhaloalkoxy radical, are most particularly preferred. The compounds of the general formula (I) in which $R^1$ represents a substituted biphenyl radical, for example a trifluoromethylbiphenyl or methyltrifluoromethoxybiphenyl radical, are more particular preferred.

A preferred subgroup of compounds consists of compounds of the general formula (I) in which G represents the radical g1, with Y representing an oxygen atom, $R^1$ represents a biphenyl radical, optionally substituted by one or more alkyl radicals, preferably methyl, ethyl or propyl, and/or a trifluoromethyl or trifluoromethoxy radical, the other substituents being as defined above, the possible geometrical and/or optical isomers, epimers and various tautomeric forms, and optional oxidized forms, especially amine oxides, thereof, and the solvates and hydrates of these compounds;

and also the possible pharmaceutically acceptable salts thereof with an acid or a base, or the pharmaceutically acceptable prodrugs of these compounds.

It should be understood that the preferences for the substituents indicated in the various subgroups defined above can be combined to form other subgroups of preferred compounds of the formula (I) according to the present invention.

Particularly preferred examples of compounds according to the present invention are chosen from:

{4-[4-(1,5-dimethyl-4-phenyl-1H-imidazol-2-yl)thiazol-2-yl]piperid-1-yl}(4'-trifluoromethylbiphenyl-2-yl)methanone;

{4-[4-(1-ethyl-5-methyl-4-phenyl-1H-imidazol-2-yl)thiazol-2-yl]piperid-1-yl}(4'-trifluoromethylbiphenyl-2-yl)methanone;

{3-[4-(1-ethyl-5-methyl-4-phenyl-1H-imidazol-2-yl)thiazol-2-yl]piperid-1-yl}(4'-trifluoromethylbiphenyl-2-yl)methanone;

{4-[4-(1-ethyl-5-methyl-4-phenyl-1H-imidazol-2-yl)thiazol-2-yl]piperid-1-yl}(6-methyl-4'-trifluoromethoxybiphenyl-2-yl)methanone;

{4-[4-(1-ethyl-5-methyl-4-(pyrid-3-yl)-1H-imidazol-2-yl)thiazol-2-yl]-piperid-1-yl}(4'-trifluoromethylbiphenyl-2-yl)methanone;

{4-[4-(1-ethyl-5-methyl-4-(pyrid-2-yl)-1H-imidazol-2-yl)thiazol-2-yl]-piperid-1-yl}(4'-trifluoromethylbiphenyl-2-yl)methanone; and {4-[4-(1-ethyl-5-methyl-4-(pyrid-2-yl)-1H-imidazol-2-yl)thiazol-2-yl]-piperid-1-yl}(6-methyl-4'-trifluoromethoxybiphenyl-2-yl)methanone;

the optical isomers thereof, oxidized forms, solvates and hydrates of these compounds;

and also the possible pharmaceutically acceptable salts thereof with an acid, or the pharmaceutically acceptable prodrugs of these compounds.

The compounds of the present invention can be prepared from the compounds of the formula (II):

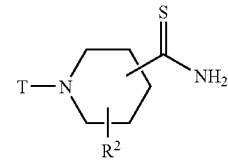

(II)

in which T represents a labile protecting group, for example tert-butoxycarbonyl (BOC), and $R^2$ is as defined above, which is reacted with ethyl $R^3$-bromopyruvate (in which $R^3$ is as defined above), generally in equimolar proportions, in a polar solvent, for example dimethylformamide, in the presence of an excess of base, preferably an organic base, such as triethylamine, at a suitable temperature, for example at room temperature, for a period ranging from 1 to 40 hours and preferably between 4 and 18 hours, so as to form the thiazolyl ring and give the compound of the formula (III):

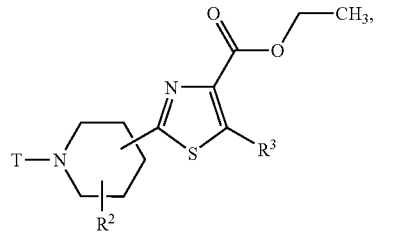

(III)

in which T, $R^2$ and $R^3$ are as defined above, which compound of the formula (III) is then saponified with a base, of alkali metal or alkaline-earth metal hydroxide type, for example sodium hydroxide, in polar medium, for instance tetrahydrofuran and/or water, especially a 2:1 tetrahydrofuran/water mixture, at room temperature, for a period ranging from 1 to 12 hours, so as to form the salt of the formula (IV):

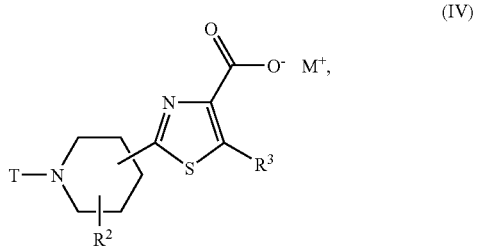

(IV)

in which T, R² and R³ are as defined above, and M⁺ represents the alkali metal or alkaline-earth metal cation derived from the base that is useful for the saponification reaction, which compound of the formula (IV) is next hydrolysed to a compound of the formula (V):

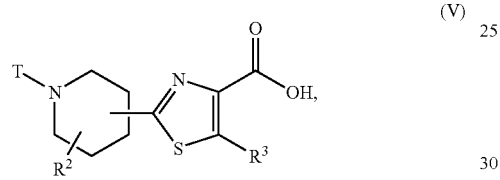

(V)

in which R², R³ and T are as defined above, which compound of the formula (V) is then converted to a corresponding amide of the formula (VI):

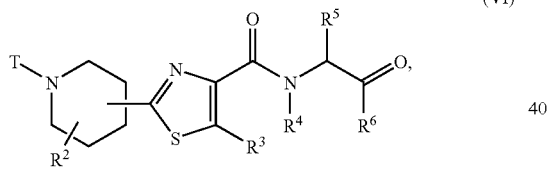

(VI)

in which R², R³, R⁴, R⁵, R⁶ and T are as defined above,
via the action of an amine of the formula (VIa):

(VIa)

in which R⁴, R⁵ and R⁶ are as defined above, generally in equimolar proportions, in the presence of a base, preferably an organic base, such as diisopropylethylamine (DIPEA), and a catalyst, for example O-benzotriazol-1-yl-N,N,N',N'-tetraethyluronium hexafluorophosphate (HBTU), in a polar aprotic solvent, such as dimethylformamide, at room temperature, for a period possibly ranging from 1 to 50 hours and generally from 4 to 20 hours, the compound of the formula (VI) then being used in a reaction for deprotection of the amine function of the piperidine ring, via the action of an organic or mineral acid, for example hydrochloric acid or trifluoroacetic acid, in dichloromethane (DCM) or dioxane medium, at room temperature, for a period ranging from a few minutes to several hours, generally ranging from 5 minutes to 12 hours, to give the compound of the formula (VII):

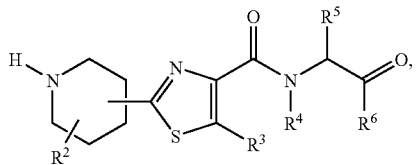

(VII)

in which R², R³, R⁴, R⁵ and R⁶ are as defined above,
which compound of the formula (VII) is then subjected to the action of a compound chosen from:

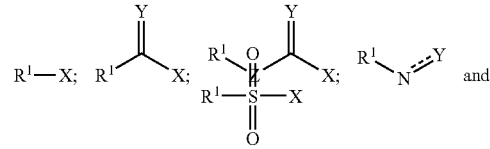

and in which X represents a halogen atom, preferably chlorine, R¹, Y and Z being as defined above,
in the presence of a base, preferably an organic base, such as diisopropylethylamine (DIPEA), and a catalyst, for example O-benzotriazol-1-yl-N,N,N', N'-tetraethyluronium hexafluorophosphate (HBTU), in a polar aprotic solvent, such as dimethylformamide, at room temperature, for a period possibly ranging from 1 to 50 hours and generally from 4 to 20 hours,
to give the compound of the formula (VIII):

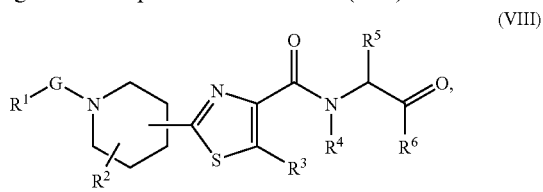

(VIII)

in which G, R¹, R², R³, R⁴, R⁵ and R⁶ are as defined above,
which is finally subjected to a cyclization reaction (formation of the imidazole ring), in the presence of a cyclizing agent, such as ammonium trifluoroacetate, also acting as solvent, at a suitable temperature, for example in the region of 150° C., for a period generally of between 5 and 15 minutes, to give the compound of the formula (I) as defined above.

According to one variant, the compounds of the formula (I) can also be prepared by reacting a compound of the formula chosen from:

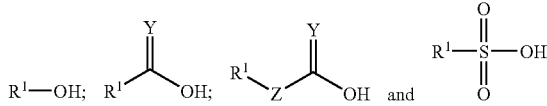

and in which R1, Y and Z are as defined above,
with a compound of the formula (IX):

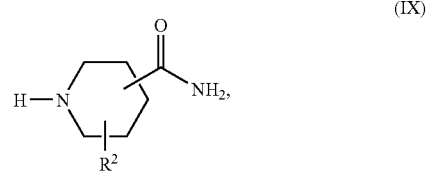

(IX)

in which R² is as defined above, in the presence of an acyl chloride, such as oxalyl chloride, in basic medium, for example triethylamine, and in an apolar aprotic solvent, for example dichloromethane, at room temperature, for a period ranging from 1 to 50 hours and generally from 4 to 20 hours, to give the compound of the formula (X):

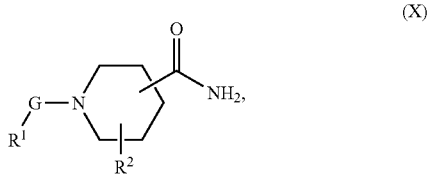

(X)

in which G, $R^1$ and $R^2$ are as defined above, which is then converted into the corresponding thioamide of the formula (XI) via the action of Lawesson's reagent, in a polar solvent, for example dimethyl ether, at a temperature of about 50° C., for a period generally of about 2.5 hours:

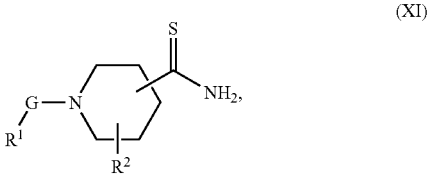

(XI)

in which G, $R^1$ and $R^2$ are as defined above, the thiazole ring then being formed in a manner similar to that presented above for the formation of the compound of the formula (III), via the action of ethyl $R^3$-bromopyruvate (in which $R^3$ is as defined above), to give the compound of the formula (XII):

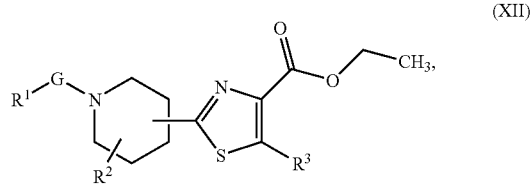

(XII)

in which G, $R^1$, $R^2$ and $R^3$ are as defined above, which compound of the formula (XII) is then saponified, in a manner similar to that for the formation of the compound of the formula (IV), to give the acid of the formula (XIII):

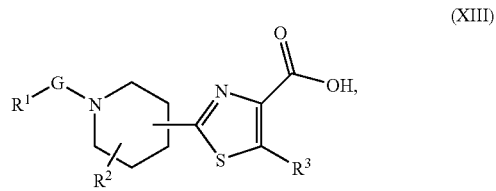

(XIII)

in which G, $R^1$, $R^2$ and $R^3$ are as defined above, which compound of the formula (XIII) is then subjected to the action of an amine of the formula (VIa) as defined above, in order to give the compounds of the formula (VIII) defined above, which are finally cyclized, as indicated above, to give the compounds of the formula (I).

In the processes described above, it should be understood that the operating conditions may vary substantially as a function of the different substituents G, $R^1$, $R^2$, $R^3$, $R^4$, $R^5$ and $R^6$ present in the compounds of the formula (I) that it is desired to prepare. Such variations and adaptations are readily accessible to a person skilled in the art, for example from scientific reviews, the patent literature, Chemical Abstracts, and computer databases, including the Internet.

The amine of the formula (VIa):

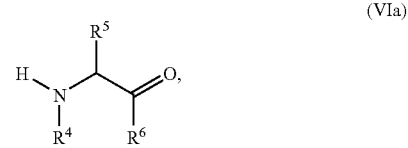

(VIa)

in which $R^4$, $R^5$ and $R^6$ are as defined for the compounds of the formula (I), can advantageously be prepared according to one of the synthetic routes presented in the following scheme, and in which the various substituents are as defined in the present invention:

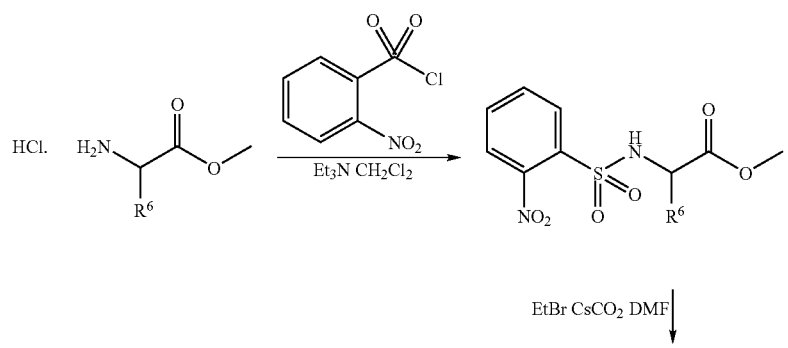

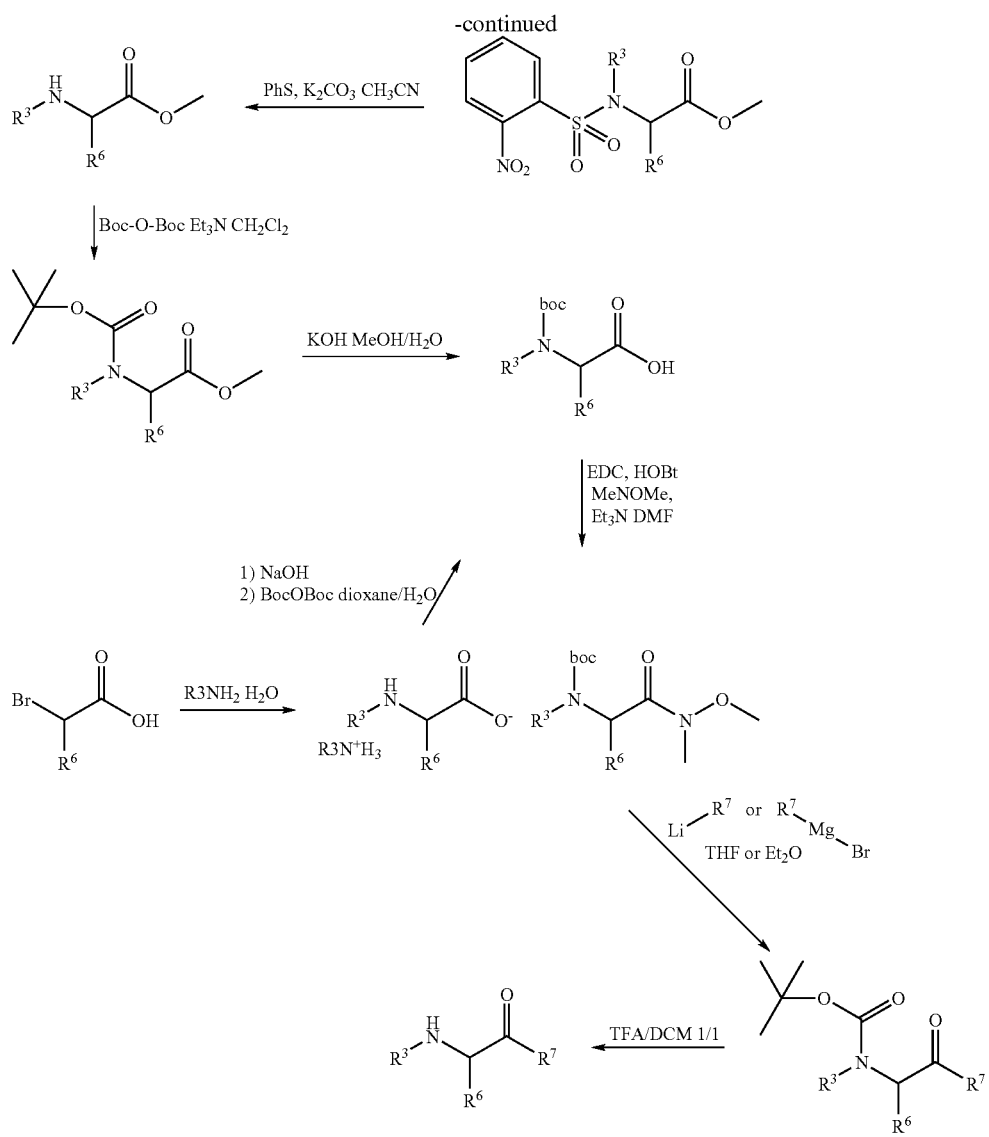

The present invention also relates to pharmaceutical compositions comprising an effective pharmaceutical amount of at least one compound of the formula (I), as defined above, in combination with one or more pharmaceutically acceptable excipients and/or vehicles.

These compositions can be administered orally in the form of immediate-release or controlled-release tablets, gel capsules or granules, intravenously in the form of an injectable solution, transdermally in the form of an adhesive transdermal device, or locally in the form of a solution, cream or gel.

A solid composition for oral administration is prepared by adding to the active principle a filler and, where appropriate, a binder, a disintegrant, a lubricant, a colorant or a flavour enhancer, and by forming the mixture into a tablet, a coated tablet, a granule, a powder or a capsule.

Examples of fillers include lactose, corn starch, sucrose, glucose, sorbitol, crystalline cellulose and silicon dioxide, and examples of binders include poly(vinyl alcohol), poly(vinyl ether), ethylcellulose, methylcellulose, acacia, gum tragacanth, gelatine, Shellac, hydroxypropylcellulose, hydroxypropylmethylcellulose, calcium citrate, dextrin and pectin.

Examples of lubricants include magnesium stearate, talc, polyethylene glycol, silica and hardened plant oils. The colorant may be any colorant permitted for use in medicaments.

Examples of flavour enhancers include cocoa powder, mint in herb form, aromatic powder, mint in oil form, borneol and cinnamon powder. It should be understood that the tablet or granule may be suitably coated with sugar, gelatine or the like.

An injectable form comprising the compound of the present invention as active principle is prepared, where appropriate, by mixing the said compound with a pH regulator, a buffer agent, a suspension agent, a solubilizer, a stabilizer, a tonicity agent and/or a preserving agent, and by converting the mixture into a form for intravenous, subcutaneous or intramuscular injection, according to a conventional process. Where appropriate, the injectable form obtained may be lyophilized via a conventional process.

Examples of suspension agents include methylcellulose, polysorbate 80, hydroxyethylcellulose, acacia, powdered gum tragacanth, sodium carboxymethylcellulose and polyethoxylated sorbitan monolaurate.

Examples of solubilizers include castor oil solidified with polyoxyethylene, polysorbate 80, nicotinamide, polyethoxylated sorbitan monolaurate and the ethyl ester of castor oil fatty acid.

In addition, the stabilizer includes sodium sulfite, sodium metasulfite and ether, while the preserving agent includes methyl para-hydroxybenzoate, ethyl para-hydroxybenzoate, sorbic acid, phenol, cresol and chlorocresol.

The compounds of the formula (I) and the pharmaceutical compositions according to the present invention are useful as microsomal triglyceride transfer protein (MTP) inhibitors.

Thus, the present invention also relates to the use of a compound of the formula (I) or a pharmaceutical composition as defined above, for the preparation of a medicament that is a microsomal triglyceride transfer protein inhibitor.

More specifically, a subject of the present invention is the use of a compound of the formula (I) or of a pharmaceutical composition as defined above for the preparation of a medicament for the prevention and/or treatment of diabetes-related hypercholesterolaemia, hypertriglyceridaemia, hyperlipidaemia, pancreatitis, hyperglycaemia, obesity, atherosclerosis and dyslipidaemia.

The compounds according to the present invention also have an inhibitory activity on the secretion of the B apoproteins (apo B). In this respect, a subject of the present invention is also the use of a compound of the formula (I) or of a pharmaceutical composition as defined above, for the preparation of a medicament for inhibiting the secretion of the B apoproteins (apo B).

The examples that follow illustrate the present invention without limiting it in any way.

EXAMPLES OF THIAZOLYLIMIDAZOLE COMPOUNDS ACCORDING TO THE INVENTION

Example 1

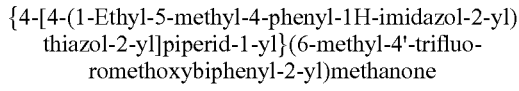
{4-[4-(1-Ethyl-5-methyl-4-phenyl-1H-imidazol-2-yl)thiazol-2-yl]piperid-1-yl}(6-methyl-4'-trifluoromethoxybiphenyl-2-yl)methanone Step a)

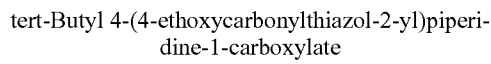
tert-Butyl 4-(4-ethoxycarbonylthiazol-2-yl)piperidine-1-carboxylate tert-Butyl 4-(aminocarbothioyl)tetrahydropyridine-1(2H)-carboxylate (Maybridge) (85 mmol; 20.8 g) is dissolved in 250 ml of dimethylformamide and placed at 5° C. Ethyl bromopyruvate (1 eq.; 85 mmol; 16.6 g) dissolved in 50 ml of dimethylformamide is added dropwise. The reaction medium is stirred overnight and excess triethylamine is then added dropwise.

The reaction medium is evaporated and the residual brown oil is taken up in ethyl acetate and washed with water (twice) and then with saturated sodium chloride solution (twice). The organic phase is dried over sodium sulfate and evaporated to dryness. The crude product is chromatographed on silica, eluting with dichloromethane to dichloromethane/3% metha nol, to give 20.5 g of the expected product in the form of oily crystals. TLC: 1/1 ethyl acetate/hexane: Rf=0.55
Yield=71%.

Step b)

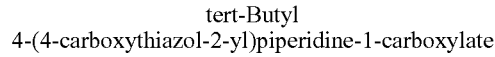
tert-Butyl 4-(4-carboxythiazol-2-yl)piperidine-1-carboxylate tert-Butyl 4-(4-ethoxycarbonylthiazol-2-yl)piperidine-1-carboxylate (60 mmol; 20.4 g) is dissolved in 225 ml of a mixture of tetrahydrofuran and water (2/1), and 1N sodium hydroxide (2 eq.; 120 mmol; 120 ml) is added dropwise.

The reaction medium is stirred at room temperature overnight.

The reaction medium is washed with ether and the aqueous phase is then acidified with saturated nitric acid solution. The precipitate is filtered off, washed with water and dried to give 15.5 g of cream-coloured crystals.
TLC: 1/1/1 $CH_2Cl_2$/EtOAc/MeOH: Rf=0.6.
Yield: 83%.

Step c)

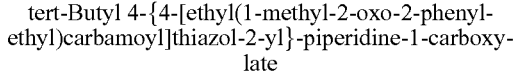
tert-Butyl 4-{4-[ethyl(1-methyl-2-oxo-2-phenylethyl)carbamoyl]thiazol-2-yl}-piperidine-1-carboxylate tert-Butyl 4-(4-carboxythiazol-2-yl)piperidine-1-carboxylate (6.5 mmol; 2.03 g) is dissolved in 40 ml of anhydrous dimethylformamide and placed under an inert atmosphere, and 2-(ethylamino)propiophenone hydrochloride (1 eq.; 6.5 mmol; 1.39 g), HBTU (1 eq.; 6.5 mmol; 2.47 g) and N-ethyldiisopropylamine (3.5 eq.; 22.75 mmol; 3.97 ml) are then added.

The reaction medium is stirred at room temperature overnight.

The reaction medium is evaporated to dryness and then taken up in dichloromethane and washed with saturated potassium carbonate ($K_2CO_3$) solution, citric acid solution and water (twice). The organic phase is dried over sodium sulfate and then evaporated to dryness. The crude product is chromatographed on silica, using a 1/1 ethyl acetate/hexane mixture as eluent (Rf=0.55) to give 2.6 g of expected product in the form of an oil.
Yield: 85%.

Step d)

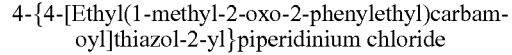
4-{4-[Ethyl(1-methyl-2-oxo-2-phenylethyl)carbamoyl]thiazol-2-yl}piperidinium chloride tert-Butyl 4-{4-[ethyl(1-methyl-2-oxo-2-phenylethyl)carbamoyl]thiazol-2-yl}-piperidine-1-carboxylate (5.5 mmol; 2.59 g) is dissolved in 13.75 ml of a 4M solution of hydrochloric acid in dioxane.

The reaction medium is stirred at room temperature overnight and is then evaporated to dryness to give 2.24 g of a white solid.
Yield=quantitative.

Step e)

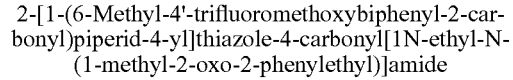
2-[1-(6-Methyl-4'-trifluoromethoxybiphenyl-2-carbonyl)piperid-4-yl]thiazole-4-carbonyl[1N-ethyl-N-(1-methyl-2-oxo-2-phenylethyl)]amide The title compound was obtained according to a procedure similar to that used for the preparation of tert-butyl 4-{4-[ethyl(1-methyl-2-oxo-2-phenylethyl)carbamoyl]thiazol-2-yl}piperidine-1-carboxylate.

TLC: 1/1 CH$_2$Cl$_2$/EtOAc: Rf=0.47 LC-MS: (ES+) 650.4 (M+H) Yield: 88%.

Step f

{4-[4-(1-Ethyl-5-methyl-4-phenyl-1H-imidazol-2-yl)thiazol-2-yl]piperid-1-yl}(6-methyl-4'-trifluoromethoxybiphenyl-2-yl)methanone 2-[1-(6-Methyl-4'-trifluoromethoxybiphenyl-2-carbonyl)piperid-4-yl]thiazole-4-carbonyl[N-ethyl-N-(1-methyl-2-oxo-2-phenylethyl)]amide (0.195 g; 0.3 mmol) is mixed with ammonium trifluoroacetate (10 eq.; 3.0 mmol; 393 mg) under a nitrogen atmosphere. The mixture is heated for 5 minutes at 150° C. with stirring, the heating is removed and water is added.

The reaction medium is then extracted twice with ethyl acetate, and the organic phases are then combined and washed with water, dried over sodium sulfate and then evaporated to dryness to give 0.171 g of a pure white solid, corresponding to the expected product.

TLC: 1:1 CH$_2$Cl$_2$/EtOAc; Rf=0.48 MS: ES+ 632.6 Yield: 90%

Examples 2 to 7

The compounds of Examples 2 to 7, presented in Table I below, were prepared in a similar manner.

TABLE 1

| Compound | R$^1$ | G | R$^2$ | R$^3$ | R$^4$ | R$^5$ | R$^6$ |
|---|---|---|---|---|---|---|---|
| 2 | 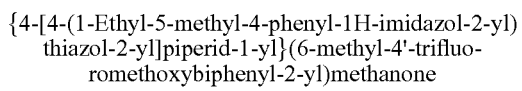 | ![ketone] | —H | —H | —CH$_3$ | —CH$_3$ | —C$_6$H$_5$ |
| 3 | (same biphenyl-OCF$_3$ group) | ![ketone] | —H | —H | —C$_2$H$_5$ | —CH$_3$ | —C$_6$H$_5$ |
| 4 | (same biphenyl-OCF$_3$ group) | ![ketone] | —H | —H | —C$_2$H$_5$ | —CH$_3$ | (3-pyridyl) |

TABLE 1-continued

| Compound | R¹ | G | R² | R³ | R⁴ | R⁵ | R⁶ |
|---|---|---|---|---|---|---|---|
| 5 | 4-(trifluoromethyl)-2'-methylbiphenyl | C=O (acetyl) | —H | —H | —$C_2H_5$ | —$CH_3$ | 2-pyridyl |
| 6 | 4-(trifluoromethoxy)-2'-methyl-6'-methylbiphenyl | C=O (acetyl) | —H | —H | —$C_2H_5$ | —$CH_3$ | 2-pyridyl |
| 7* | 4-(trifluoromethyl)-2'-methylbiphenyl | C=O (acetyl) | —H | —H | —$C_2H_5$ | —$CH_3$ | —$C_6H_5$ |

*In the compound of Example 7, the thiazole nucleus is branched in position 3 of the piperidine ring. For all the other examples (1 to 6), the thiazole nucleus is branched in position 4 of the piperidine ring.

The results of the spectral analyses (NMR or mass) of the compounds of Examples 1 to 7 are as follows:

| Compound | ¹H NMR | Mass |
|---|---|---|
| 1 | | ES+ 632.6 |
| 2 | δ ppm (CDCl₃): 1.41-3.53 (14H, m); 4.48-4.87 (1H, m); 6.80-8.25 (14H, m). | |
| 3 | δ ppm (CDCl₃): 1.23-2.14 (m, 7H); 2.23-3.46 (m, 4H); 2.37-2.47 (m, 3H); 4.25-4.81 (m, 3H); 7.25-7.78 (m, 14H). | |
| 4 | | ES+ 602.4 |
| 5 | | ES+ 602.5 |
| 6 | | ES+ 632.6 |
| 7 | δ ppm (DMSO-d6): 0.78-4.77 (17H, m); 7.07-8.08 (14H, m). | |

BIOLOGICAL EXPERIMENTAL SECTION

Biological Activity Tests

Analysis of the Inhibition of MTP Activity

The inhibition of the activity of microsomal triglyceride transfer protein (MTP) was tested by using the following operating protocol.

The inhibition of MTP activity with a compound can be quantified by observing the inhibition of the transfer of a labelled triglyceride, from a donor particle to an acceptor particle, in the presence of MTP. The procedure for the preparation of MTP is based on the method by Wetterau and Zilversmit (*Biochem. Biophys. Acta* (1986) 875, 610). A few grams of golden hamster liver are taken and then rinsed several times in a 250 mM sucrose solution at 0° C. All the following steps proceed at +4° C. A homogenate at a concentration of 50% in 250 mM sucrose is prepared using a Teflon mill and then centrifuged for 10 minutes at 10 000×g at +4° C. The supernatant is then centrifuged at 105 000×g for 75 minutes at +4° C. The supernatant is discarded and the microsomal pellet is taken up in 3 ml (per g of starting liver) of Tris/HCl 150 mM pH 8.0. 1 ml aliquot fractions are stored at −80° C. until the time of use.

After thawing a fraction of microsomes (1 ml), 12 ml of refrigerated Tris/HCl 50 mM, KCl 50 mM, MgCl$_2$ 5 mM pH 7.4 buffers and 1.2 ml of deoxycholate (0.54% in water) are added. After incubation for 30 minutes at +4° C. with gentle agitation, the suspension is centrifuged at 105 000×g for 75 minutes. The supernatant comprising the soluble MTP is dialysed against Tris/HCl 150 mM, NaCl 40 mM, EDTA 1 mM, 0.02% sodium azide pH 7.4 buffer (5 times one litre over 2-3 days). The MTP is stored at +4° C., is stable for at least 30 days and is used in unmodified form in the test.

The donor particles (liposomes) are prepared from 208 µl of L-phosphatidylcholine at a concentration of 10 mg/ml in chloroform, and 480 µl of [3H]-triolein at a concentration of 0.5 mCi/ml in toluene. After stirring, the solution is evaporated under nitrogen, taken up in 6 ml of Tris/HCl 50 mM, KCl 50 mM, MgCl$_2$ 5 mM pH 7.4 buffer and incubated in an ultrasound bath for 30 minutes at room temperature. The liposomes are stored at +4° C. and sonicated again for 10 minutes before each use.

The acceptor particles are biotinylated low density lipoproteins (LDL-biot). These particles are supplied by the company Amersham.

The reaction mixture is prepared in untreated ½ well white plates (Corning Costar) by addition, in the following order, of: 5 µl of HEPES 50 mM, NaCl-150 mM, BSA 0.1% (w/v), 0.05% sodium azide (w/v), pH 7.4 buffer; 5 µl of liposomes; 5 µl of LDL-biot; 5 µl of test products in DMSO; 5 µl of MTP. After incubation for 18-24 hours at 37° C., the reaction is stopped by adding 100 µl of Amersham SPA (scintillation proximity assay) beads coupled to streptavidin, and the radioactivity is counted using a Top Count (Packard) machine at least one hour later. The inhibition of the transfer of the triglycerides with a compound is reflected by a reduction in the transferred radioactivity. The percentage inhibition for a given compound is determined relative to controls that do not comprise compounds in the reaction mixture.

The results are expressed in terms of the $IC_{50}$, i.e. the concentration that allows a 50% inhibition of MTP. These results are summarized in Table A below for a number of representative compounds of the invention.

TABLE A

| Example | $IC_{50}$ (nM) |
| --- | --- |
| 1 | 320.00 |
| 2 | 300.00 |
| 3 | 270.00 |
| 4 | 816.00 |
| 5 | 2542.00 |
| 6 | 1830.00 |

Analysis of the Secretion of Apo B in the HepG2 Human Cell Line:

The activity of a compound according to the invention can be evaluated by measuring the inhibition of apo B secretion in HepG2 cells.

The HepG2 cells (ECACC-No. 85011430) are used as model in the study of the in vitro hepatic secretion of lipoproteins (Dixon J. and Ginsberg H., *J. Lipid. Res.*, 1993, 34, 167-179).

The HepG2 cells are cultured in Dulbecco's modified Eagle's medium comprising 10% foetal calf serum (DMEM and FBS-Gibco) in 96-well plates under an atmosphere of 5% carbon dioxide for 24 hours (about 70% confluence).

The test compounds are dissolved at a concentration of 2 or 10 mM in dimethyl sulfoxide (DMSO). Serial dilutions (1:3.16) are made in DMSO and are:added (1:200—Robot Multimek Beckman) to the growth medium (200 µl) and then finally incubated for 24 hours in the various wells containing the HepG2 cells.

The 24-hour culture supernatant diluted to 1:5 (phosphate-buffered saline: PBS comprising 1% bovine serum albumin) is tested according to a sandwich-ELISA method specific for human apo B.

The results are expressed in terms of $IC_{50}$, i.e. the concentration that produces a 50% inhibition of apo B secretion in the HepG2 cells.

These results are collated in Table B below for a number of representative compounds of the invention.

TABLE B

| Example | $IC_{50}$ (nM) |
| --- | --- |
| 1 | 369.00 |
| 2 | 616.00 |
| 3 | 390.00 |
| 4 | 1573.00 |
| 5 | 2624.00 |
| 6 | 2297.00 |
| 7 | 2088.00 |

The invention claimed is:

1. {4-[4-(1,5-dimethyl-4-phenyl-1H-imidazol-2-yl)thiazol-2-yl]piperid-1-yl}(4'-trifluoromethylbiphenyl-2-yl) methanone;
 -{4-[4-(1-ethyl-5-methyl-4-phenyl-1H-imidazol-2-yl) thiazol-2-yl]piperid-1-yl}(4'-trifluoromethylbiphenyl-2-yl)methanone;
 -{3-[4-(1-ethyl-5-methyl-4-phenyl-1H-imidazol-2-yl) thiazol-2-yl]piperid-1-yl}(4'-trifluoromethylbiphenyl-2-yl)methanone;
 -{4-[4-(1-ethyl-5-methyl-4-phenyl-1H-imidazol-2-yl) thiazol-2-yl]piperid-1-yl}(6-methyl-4'-trifluoromethoxybiphenyl-2-yl)methanone;
 -{4-[4-(1-ethyl-5-methyl-4-(pyrid-3-yl)-1H-imidazol-2-yl)thiazol-2-yl]piperid-1-yl}(4'-trifluoromethylbiphenyl-2-yl)methanone;
 -{4-[4-(1-ethyl-5-methyl-4-(pyrid-2-yl)-1H-imidazol-2-yl)thiazol-2-yl]piperid-1-yl}(4'-trifluoromethylbiphenyl-2-yl)methanone;
 -{4-[4-(1-ethyl-5-methyl-4-(pyrid-2-yl)-1H-imidazol-2-yl)thiazol-2-yl]piperid-1-yl}(6-methyl-4'-trifluoromethoxybiphenyl-2-yl)methanone;
 or an optical isomer, epimer, tautomer, amine oxide, hydrate, pharmaceutically acceptable salt with an acid or a base.

2. A pharmaceutical composition comprising a pharmaceutically effective amount of a compound of claim 1, in combination with one or more pharmaceutically acceptable vehicles.

3. A method for the treatment of diabetes-related hypertriglyceridaemia, hypercholesterolaemia, dyslipidaemia, or for treatment of obesity, comprising administering to a host in need thereof an effective amount of a compound of claim 1.

* * * * *

UNITED STATES PATENT AND TRADEMARK OFFICE
CERTIFICATE OF CORRECTION

PATENT NO. : 7,767,819 B2
APPLICATION NO. : 10/587975
DATED : August 3, 2010
INVENTOR(S) : Guedat et al.

It is certified that error appears in the above-identified patent and that said Letters Patent is hereby corrected as shown below:

Column 22, line 53 reads, "hydrate. pharmaceutically acceptable salt with an acid," SHOULD READ --hydrate, or pharmaceutically acceptable salt with an acid--

Signed and Sealed this

Twenty-eighth Day of September, 2010

David J. Kappos
*Director of the United States Patent and Trademark Office*